United States Patent
Ciok et al.

(10) Patent No.: US 7,160,274 B2
(45) Date of Patent: Jan. 9, 2007

(54) SKIN-CLEANSING APPLIANCE WITH VENTING APERATURES

(75) Inventors: Danuta Ciok, Niva (DK); Dorrit Diana Israelson, Gentofte (DK)

(73) Assignee: Coloplast A/S, Humlebaek (DK)

( * ) Notice: Subject to any disclaimer, the term of this patent is extended or adjusted under 35 U.S.C. 154(b) by 177 days.

(21) Appl. No.: 10/451,638

(22) PCT Filed: Jan. 28, 2002

(86) PCT No.: PCT/DK02/00063

§ 371 (c)(1),
(2), (4) Date: Jul. 10, 2003

(87) PCT Pub. No.: WO03/032877

PCT Pub. Date: Apr. 24, 2003

(65) Prior Publication Data

US 2004/0054339 A1 Mar. 18, 2004

(30) Foreign Application Priority Data

Jan. 26, 2001 (DK) ............................... 2001 00141

(51) Int. Cl.
*A61F 5/445* (2006.01)
*A61L 24/00* (2006.01)

(52) U.S. Cl. .................. 604/332; 604/305; 604/337

(58) Field of Classification Search ................ 604/290, 604/275–277, 332, 334, 337–344, 305, 310; 600/156; 134/104.1
See application file for complete search history.

(56) References Cited

U.S. PATENT DOCUMENTS

| | | | |
|---|---|---|---|
| 1,597,556 A | 8/1926 | Townsend | |
| 2,679,248 A * | 5/1954 | Fullaway | 604/332 |
| 3,910,274 A * | 10/1975 | Nolan | 604/277 |
| 4,004,589 A | 1/1977 | Neumeier | 128/245 |
| 4,318,406 A * | 3/1982 | McLeod | 604/333 |
| 4,367,742 A | 1/1983 | Ornstein | 128/283 |
| 4,445,898 A * | 5/1984 | Jensen | 604/337 |
| 4,586,927 A | 5/1986 | Jensen | 604/342 |
| 4,588,397 A | 5/1986 | Giacalone | 604/349 |
| 4,654,037 A * | 3/1987 | Fenton | 604/334 |
| 4,668,227 A | 5/1987 | Kay | 604/289 |
| 4,723,951 A * | 2/1988 | Steer | 604/333 |
| 4,810,250 A * | 3/1989 | Ellenberg et al. | 604/277 |
| 5,051,259 A | 9/1991 | Olsen et al. | 424/443 |

(Continued)

FOREIGN PATENT DOCUMENTS

WO 93/18725 9/1993

(Continued)

*Primary Examiner*—Tatyana Zalukaeva
*Assistant Examiner*—Laura C. Hill
(74) *Attorney, Agent, or Firm*—Jacobson Holman PLLC

(57) ABSTRACT

An appliance for cleansing a surface area of the skin including a separately applicable cleansing appliance adapted to fit tightly against the surface of the body and being provided with an inlet for injection of liquid and an outlet. The appliance includes two walls of flexible material, with the rear wall having an opening suitable for surrounding the surface area of the skin to be cleansed. The front wall is provided with an adapter secured sealingly to the wall, with an opening in the front wall giving access to the internal space between the front and rear walls through the adapter. A plurality of holes separate from the openings in the front and rear walls create a venturi effect to reduce the risk that a vacuum may tend to draw the front wall against the rear wall and cause the bag to collapse.

16 Claims, 2 Drawing Sheets

U.S. PATENT DOCUMENTS

| | | | |
|---|---|---|---|
| 5,133,701 A | 7/1992 | Han | 604/289 |
| 5,236,426 A | 8/1993 | Schöttes et al. | 604/33.4 |
| 5,250,043 A * | 10/1993 | Castellana et al. | 604/336 |
| 5,470,325 A * | 11/1995 | Fundock | 604/332 |
| 5,496,297 A | 3/1996 | Olsen | 604/339 |
| 5,714,225 A | 2/1998 | Hansen et al. | 428/114 |
| 5,738,661 A | 4/1998 | Larice | 604/180 |
| 5,800,415 A | 9/1998 | Olsen | 604/336 |
| 6,206,864 B1 * | 3/2001 | Kavanagh et al. | 604/332 |
| 6,224,581 B1 * | 5/2001 | Withers et al. | 604/334 |
| 6,245,049 B1 | 6/2001 | Samuelsson | 604/276 |
| 6,595,971 B1 * | 7/2003 | von Dyck et al. | 604/334 |

FOREIGN PATENT DOCUMENTS

| | | |
|---|---|---|
| WO | 94/18919 | 9/1994 |
| WO | 98/24387 | 6/1998 |
| WO | WO 9853772 A1 * | 12/1998 |

\* cited by examiner

SKIN-CLEANSING APPLIANCE WITH VENTING APERATURES

BACKGROUND OF THE INVENTION

1. Field of the Invention

The present invention relates in its broadest aspect to an appliance and a method for cleansing a surface area of the skin such as a wound, a fistula, or an artificial orifice or opening such as the end of an intestine or stoma protruding from the skin of a human body. Thus, the present invention relates to a appliance for cleansing an artificial orifice or opening in the form of the end of an intestine or a stoma and furthermore, an appliance for cleansing surface areas of the skin such as a wound or the area of a drainage site.

In connection with surgery for a number of diseases in the gastro-intestinal tract a consequence is, in many cases, that the colon, the ileum or the urethra is exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula, which has developed between an internal organ and the abdominal surface, the patient will have to rely on an appliance to collect the bodily material emerging from such opening. Collecting bags may also be used for collecting exudates from a wound or collection of bodily material in connection with post operation or drainage purposes.

Appliances for such uses are well known and may be two-piece or one-piece appliances. In both types of appliances, a body side member is attached to the wearer's abdomen, and a collecting member or bag is attached to the ostomy body side member for receiving exudates from the stoma or wound, the collecting member or bag being releasably attached in case of a two-piece appliance.

When using one-piece appliances, the whole appliance, including the adhesive wafer or pad securing the appliance to the skin is removed and replaced by a fresh appliance. When using two-piece appliances, the ostomy body side member is left in place for several days, and only the collecting member or bag is replaced.

The end of the intestine or a protruding stoma will normally be covered by an ostomy appliance for collecting the effluents or waste products of the body, which are conveyed through such artificial orifice or opening and the opening and the surrounding area must regularly be cleansed.

In connection with stomas, wounds, areas of a drainage site or fistulas it is necessary from time to time to change a dressing covering the same and it is also often desirable to rinse the stoma, wound, fistula or drainage area before applying a fresh dressing.

However, in connection with two-piece appliances, the size of the aperture of the flange of the bag is often greater than the size of the apertures of the commonly used body side members, and there is a considerable risk of access of exudates to the distal surface of the adhesive wafer of the body side member. This opens for chemical attack on the adhesive from the "back" and may furthermore give rise to soiling or contamination the distal surface of the body side member, especially in connection with colostomies. This may reduce the wearing time of the body side member and furthermore give rise to problems when substituting the collecting bag with a fresh bag as the coupling area may have to be cleaned in order to ensure a proper coupling and sealing of the fresh bag and also to ensure that residues giving rise to unpleasant odours are not left on the body side member. Altogether there is a considerable risk of having to exchange the body side member before its technical service time has been exhausted.

The same applies to collecting appliances for other purposes such as collecting exudates from a wound or collection of bodily material in connection with post operation or drainage purposes.

2. Description of the Related Art

WO 98/24387 discloses a device for cleansing the end of an intestine protruding from a human body. The cover has an elastic peripheral edge to fit tightly against the surface of the body when placed over a stoma, it is provided with an outlet at the bottom which outlet may be connected to a hose leading to the toilet bowl or other drain, and it is provided with a ball placed in a movable joint and having a through-channel for injection of liquid.

The device disclosed in WO 98/24387 suffers from the drawback that the sealing against the body is depending on the pressure with which it is pressed against the body and that the pressure must be nearly equally distributed along the periphery in order to ensure a safe sealing. Such pressure is difficult to maintain, even for e.g. a nurse cleansing the stoma area when, at the same time, she has to operate the device for allowing liquid to be sprayed over the entire surface covered by the cover. Furthermore, the device is relatively expensive and provided with movable parts and several areas being difficult to cleanse after the use, especially the top edges and the area surrounding the ball as well as the outlet and the surrounding area.

U.S. Pat. No. 4,586,927 discloses an irrigation sleeve for colostomy patients which sleeve can be removeably attached to different snap-on attachments such as an irrigation attachment or rinsing or flushing attachment. The sleeve is provided with a cone shaped body communicating with a conduit from a reservoir, said cone shaped body having the large diameter end pointing away from the patient.

U.S. Pat. No. 5,738,661 discloses a medical device for holding a feeding tube comprising a cone shaped projection for rigid fastening of the tube.

The devices disclosed in U.S. Pat. Nos. 4,586,927 and 5,738,661 do not offer an option to cleanse a surface area of the skin and none of the above-referenced publications offer any solution for avoiding a vacuum in the bag causing the same to collapse giving rise to a risk that visceral contents being cleansed away from a stoma will not immediately be able to separate the walls and "fall" into the bottom of the receiving bag but will rather stay and obstruct the cleaning process as solid pieces of visceral contents are not flushed down.

Thus, there is still a need of cleansing device for cleansing a surface area of the skin such as a wound, a fistula, or an artificial orifice or opening such as the end of an intestine or stoma protruding from the skin of a human body which device is easily operated by one person and provides a safe and reliable sealing against the body, is suitable for cleansing a surface area of the skin of a patient having a wound, a fistula, or an artificial opening such as a stoma, which device reduces the risk that a vacuum may tend to draw the front wall against the rear wall and causing the bag to collapse and which device is preferably a cheap device that may be used as a disposable device in order to avoid laborious cleansing procedures and necessary cleansing facilities.

It has been found that these needs may be fulfilled by the present invention.

SUMMARY OF THE INVENTION

The present invention relates to an appliance for cleansing a surface area of the skin which appliance is in the form of a set comprising a) a body side member comprising an adhesive wafer for securing the appliance to the patient's skin, said wafer or pad having an aperture for receiving a stoma, surrounding a wound, a fistula or a drainage site, and further having first coupling means being fixedly connected to the body side member, and b) a separately applicable cleansing appliance being adapted to fit tightly against the surface of the body and being provided with an inlet for injection of liquid and an outlet.

Furthermore, the invention relates to a cleansing appliance adapted to fit tightly against the surface of a body side member and being provided with an inlet for injection of liquid an outlet.

The invention also relates to a method of cleansing a surface area of the skin such as a wound, a fistula, or an artificial orifice or opening such as the end of an intestine or stoma protruding from the skin of a human body.

BRIEF DESCRIPTION OF THE DRAWINGS

The invention is now explained more in detail with reference to the drawings showing preferred embodiments of the invention.

DETAILED DESCRIPTION OF THE PRESENT INVENTION

Figure 1:
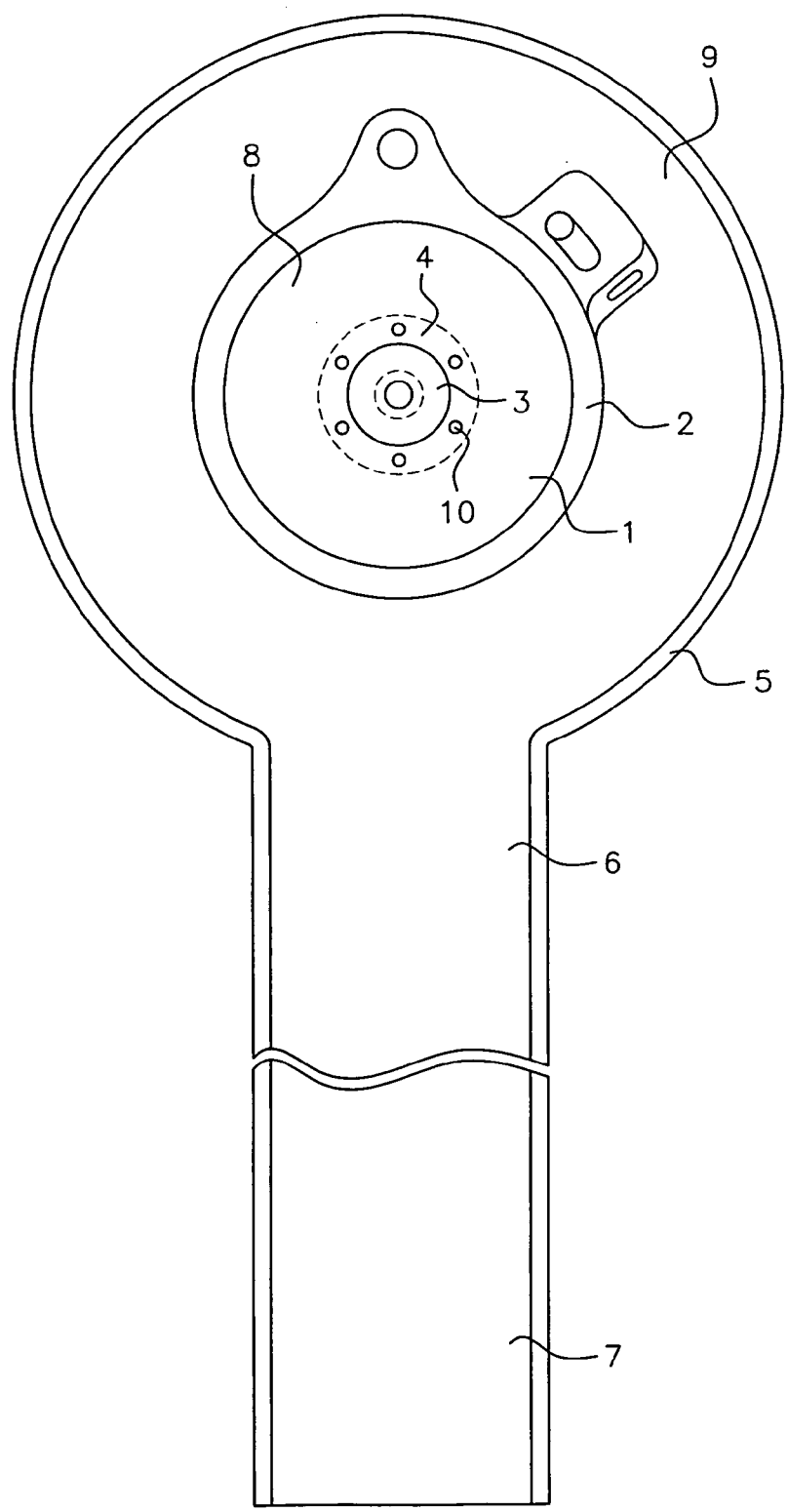
FIG. 1 shows an embodiment of a cleansing device according to the present invention provided with a coupling ring, seen from the proximal side.

The present invention relates to an appliance for cleansing a surface area of the skin which appliance is in the form of a set comprising a) a body side member comprising an adhesive wafer for securing the appliance to the patient's skin, said wafer or pad having an aperture for receiving a stoma, surrounding a wound, a fistula or a drainage site, and further having first coupling means being fixedly connected to the body side member, and b) a separately applicable cleansing appliance adapted to fit tightly against the surface of the body side member and being provided with an inlet for injection of liquid an outlet, said appliance comprising a front wall and a rear wall of flexible material defining a space there between, the rear wall having an opening suitable for surrounding the surface area of the skin to be cleansed which opening is surrounded by matching second coupling means adapted for removable coupling and sealing to first coupling means of the body side member, the front wall being provided with an adapter secured sealingly to the wall and having an opening communicating with an inlet opening in the front wall giving access to the internal space between the front and back walls through the adapter which adapter is suitable for being connected to a supply for cleansing liquid, and an outlet opening, wherein the adapter has essentially conical shape and wherein the top and narrow part of the cone is directed away from the patient.

The cleansing device of the invention is easily operated by one person as it is provided with coupling means sealingly securing the device against the surface of the body leaving both hands of the person free to operate the device. Thus, an assisting person such as a nurse is not needed for a patient having sufficient dexterity to operate the device. Furthermore, as the front wall of the device is flexible and provided with an adapter secured sealingly to the wall and having an opening communicating with an inlet opening in the wall, the inlet adapter easily may be manoeuvred to clean all parts of the area in question, even partly the inner surfaces of the device, and the device of the invention is far more flexible and cheaper than the device having a ball placed in a movable joint as disclosed in WO 98/24387 and still further, movable parts are avoided. The device of the invention may be produced from standard materials normally used for preparation of disposable ostomy, wound and incontinence devices and it is thus possible to provide a cheap disposable cleansing device rendering laborious cleansing procedures and necessary cleansing facilities superfluous. Furthermore, there is a reduced risk of escape of noxious smells, the device is small, flexible and easy to handle and timesaving in use as compared to the device disclosed in WO 98/24387.

The set of the invention is suitable for cleansing a surface area of the skin of a patient having a wound, a fistula, or an artificial orifice or opening such as the end of an intestine or stoma protruding from the skin of a human body which surface area is bandaged using a disposable dressing such as a one-piece ostomy appliance or a conventional wound dressing. A preferred use is as ostomy cleansing appliances or cleansing appliances for wound care purposes, mostly preferred as ostomy cleansing appliances.

The cleansing device of the invention may be produced from standard materials normally used for preparation of disposable ostomy and wound and incontinence devices. Thus, the adhesive wafer may be made from a medical grade barrier adhesives known in the such as the formulation being disclosed, for example in U.S. Pat. Nos. 4,367,732, 5,051,259 or 5,714,225.

The coupling means may suitably be matching coupling rings of the type disclosed in WO 93/18725 or WO 94/18919 or matching flanges for adhesive connection of the type disclosed in U.S. Pat. No. 5,800,415.

The two walls mentioned may be of any plastic sheet material normally used in connection with ostomy equipment, in particular ostomy bags; the only special condition being that the material should be compatible with the plastics material of the adapter and the coupling means in order to enable combination by gluing or welding in a manner known per se.

The adapter providing a connection between the appliance of the invention and a source for cleansing liquid, e.g. a tube, will suitably be made from a relatively rigid polymer such as polyethylene or a copolymer thereof, e.g. an EVA or styrene and ethylene/butylene copolymer and will be apt for coupling to e.g. a hose for supplying cleansing liquid. The adapter may be in the form of a relatively flat or steep cone having a height of from 0.1 to 10 centimetres, preferably up to 5 centimetres or may even be flat as long as the material does not hamper the freedom of directing the cleansing jet of liquid in a desired direction. The base diameter of the adapter is suitably from 0.5 to 5 centimetres, the maximum size of the adapter being determined by the size of the front wall. If the zone for attachment of the adapter to the wall is kept at a distance inside the welding seam sealing the front and rear walls together, it is foreseen that the diameter of the adapter may be even larger which is also considered an embodiment of the invention.

The cleansing liquid may suitably be tap water.

The two walls may be heat welded together in a manner known per se for preparing urine collection or ostomy collecting bags.

One of the walls of the cleansing appliance of the invention is preferably provided with a number of holes allowing air to be drawn into the bag in order to compensate for a vacuum produced in the bag during use due to a water-jet air pump effect produced by a jet of cleansing liquid entering the device through the adapter as such vacuum may tend to draw the front wall against the rear wall and causing the bag to collapse.

In accordance with a preferred embodiment of the invention, the holes are pinholes being sufficiently large to allow air to be drawn into the cleansing appliance. Such holes should be sufficiently large to allow air to be drawn into the cleansing appliance and, at the same time, sufficiently small not to allow cleansing liquid to escape through the holes produced by the jet of water entering the bag.

Suitably, such holes have a diameter of about 0.05 to 0.4 mm, preferably 0.1 to 0.2 mm, and a larger number of small holes giving a sufficient venting are preferred as compared to a few larger holes as small holes are normally more suitable for preventing cleansing liquid from escaping from the appliance.

In accordance with a further embodiment of the invention the holes may be larger provided that they are located in vicinity of the place in which the adapter is secured, as there is then a minimum risk that liquid escapes the bag through the holes.

In a preferred embodiment the holes are located in such a relationship to the adapter so as to provide a venturi effect drawing air into the bag together with the cleansing liquid minimizing the risk of a collapse of the bag due to a vacuum. Thus, the holes may be placed outside the zone in which the adapter is secured to the wall or in the adapter itself. Such holes may e.g. have a diameter greater than 0.2 millimetres, e.g. up to 1–5 millimetres or even more depending on the actual location with respect to the liquid inlet. Suitably 4 to 10, preferably 5 to 8 such holes are present.

When using the set of the invention, firstly, the stoma, wound, fistula or drainage site of the patient is identified, then the body side member of the set of the invention comprising an adhesive wafer is secured to the patient's skin in such a manner that the aperture receives the stoma, or surrounds the area surrounding the wound, the fistula or the drainage site, the separately applicable cleansing appliance is coupled to the body side member using the matching coupling means, the inlet of the adapter is connected to a source for cleansing liquid, the outlet opening is directed to a receiving member or a drain, and the flow of cleansing liquid is activated and directed to the surfaces to be cleansed by manually moving the adapter.

The invention also relates to a cleansing device having an edge adapted to fit tightly against the surface of the body and being provided with an inlet for injection of liquid and an outlet, said appliance comprising a front wall and a rear wall of flexible material defining a space there between, the rear wall having an opening suitable for surrounding a surface area of the skin to be cleansed which opening is surrounded by coupling means adapted for removable coupling and sealing to matching coupling means of a body side member, the front wall being provided with an adapter secured sealingly to the wall and having an opening communicating with an opening in the front wall giving access to the internal space between the front and back walls through the adapter which adapter is suitable for being connected to a supply for cleansing liquid, and an outlet opening, wherein the adapter has essentially conical shape and wherein the top and narrow part of the cone is directed away from the patient.

The cleansing appliance of the invention provided with coupling means for attachment to a body side member is suitable for cleansing a surface area of the skin of a patient having a wound, a fistula, or an artificial orifice or opening such as the end of an intestine or stoma protruding from the skin of a human body which surface area is bandaged using a two-piece appliance such as a two-piece ostomy appliance having an ostomy body side member essentially permanently situated around the stoma.

When using the appliance of the invention, the procedure is analogous to the procedure described above in connection with the use of the set of the invention apart from the identification of the stoma, wound, fistula or drainage site of the patient, and securing the body side member of the set of the invention to the patient's skin in such a manner that the aperture receives the stoma, or surrounds the area surrounding the wound, the fistula or the drainage site, The invention furthermore relates to a method of cleansing a surface area of the skin such as a wound, a fistula, or an artificial orifice or opening such as the end of an intestine or stoma protruding from the skin of a human body which method comprises a) identifying the stoma, wound, fistula or drainage site of the patient, b) securing the body side member of the set of the invention comprising an adhesive wafer to the patient's skin in such a manner that the aperture receives the stoma, or surrounds the area surrounding the wound, the fistula or the drainage site, c) coupling the separately applicable cleansing appliance to the body side member using the matching coupling means, d) connecting the inlet of the adapter to a source for cleansing liquid, e) directing the outlet opening to a receiving member or a drain, and f) activating the flow of cleansing liquid and directing the same to the surfaces to be cleansed by manually moving the adapter.

Still further, the invention relates to a method of cleansing a surface area of the skin of a patient having a wound, a fistula, or an artificial orifice or opening such as the end of an intestine or stoma protruding from the skin of a human body which surface area is bandaged using a two-piece appliance such as a two-piece ostomy appliance having an ostomy body side member essentially permanently situated around the stoma which method comprises a) identifying the body side member on the skin of the patient, b) coupling the separately applicable cleansing appliance to the body side member using the matching coupling means, c) connecting the inlet of the adapter to a source for cleansing liquid,
d) directing the outlet opening to a receiving member or a drain, and
e) activating the flow of cleansing liquid and directing the same to the surfaces to be cleansed by manually moving the adapter.

The coupling means may be any suitable coupling means known per se for coupling of ostomy body side members to ostomy collecting bags, e.g. a mechanical coupling such as matching coupling rings or it may be in the form of a first flange secured to the body side member and a second flange secured to the collecting bag, the second flange being adapted for removable and adhesive coupling and sealing to the first flange.

An adhesive body side member may be made from materials conventionally used for the preparation of ostomy or continence appliances in analogy with manners known per se in the field.

A cleansing appliance of the invention may be made from materials conventionally used for the preparation of collecting bags for use in an ostomy appliance according to the invention.

In the present context, the term "front" or "distal" in connection with a surface of an appliance is used to designate the surface thereof being opposite to the skin-contacting surface thereof, and "rear" or "proximal" is used to designate the skin-contacting surface of the appliance.

DESCRIPTION OF THE PREFERRED EMBODIMENTS

The invention is now explained more in detail with reference to the drawings showing preferred embodiments of the invention. However, it should be understood that the detailed description and specific examples, while indicating preferred embodiments of the invention, are given by way of illustration only, since various changes and modifications within the spirit and scope of the invention will become apparent to those skilled in the art from this detailed description.

In FIG. 1 is shown an embodiment of an ostomy cleansing appliance of the invention comprising a front wall 8 and a rear wall 9 of a polyethylene sheet material, said rear wall having an opening 1 into the bag by which waste material can enter the appliance or bag. The opening has a coupling ring 2 made from polyethylene-EVA copolymer for engaging with a corresponding coupling ring 18 placed on an adhesive wafer 20 of a body side member. Furthermore, the appliance has an adapter 3 made from polyethylene on the front wall, said adapter being welded sealingly 4 to the front wall. The adapter 3 has an inlet 22 communicating with an opening 24 in the front wall 8. The front and rear walls are sealed along the periphery thereof by a welding seam 5 leaving an outlet 6 open. In the front wall 8 is shown 6 holes 10 having a diameter of 0.7 millimetres located in vicinity of the zone in which the adapter is secured so as to provide a venturi effect drawing air into the bag together with the cleansing liquid.

At the outlet 6 the appliance is provided with an elongated part 7 for directing the cleansing liquid from the cleansing device to a receptacle, e.g. a WC bowl. The length of the elongated part 7 may typically be from about 40 to about 120 centimetres depending on the height of the user.

The inlet 22 to the adapter may be connected to a water tap using a hose (not shown) provided with conventional coupling means for coupling to the water tap. The hose is preferably provided with a device known per se for adjusting the flow through the hose.

The adapter may be connected to a water tap using a hose (not shown) provided with conventional coupling means for coupling to the water tap. The hose is preferably provided with a device known per se for adjusting the flow through the hose.

Figure 2:
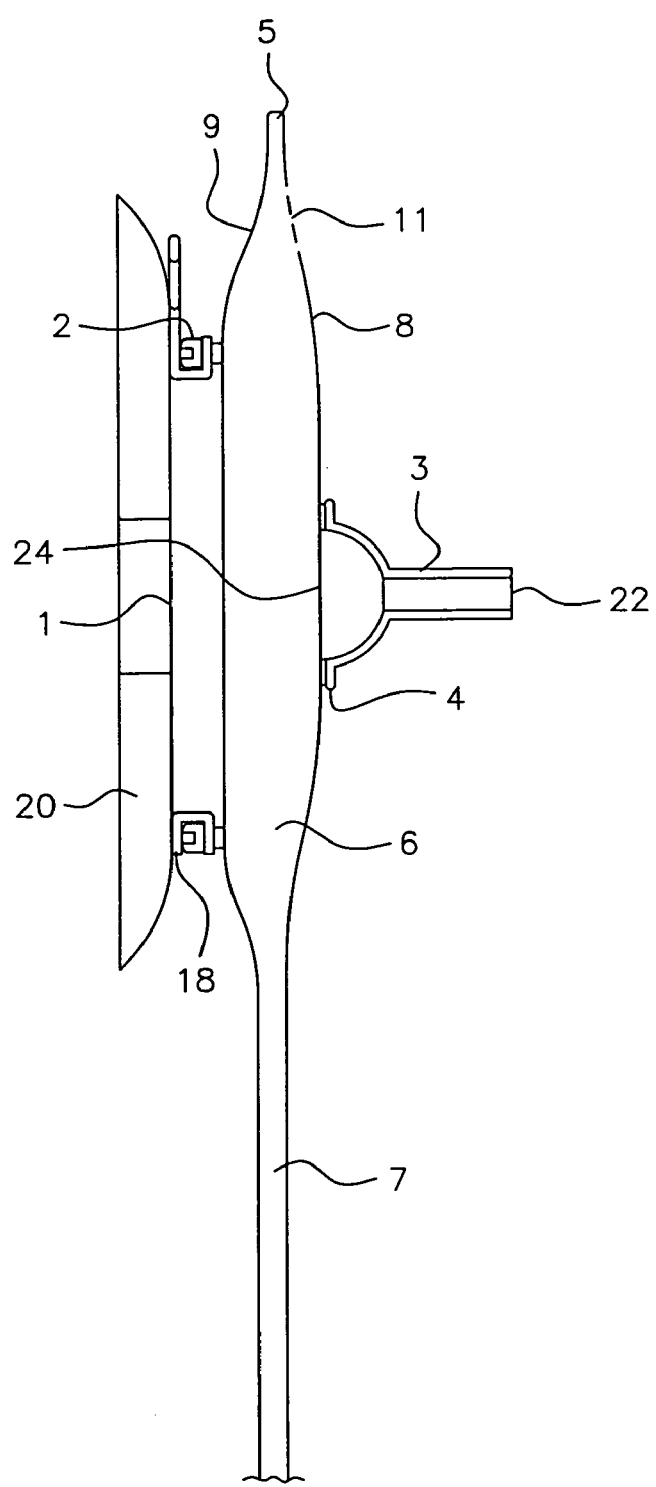
FIG. 2 shows a longitudinal section of another embodiment of the present invention.

In the embodiment shown in FIG. 2, the top of the wall 8 of the cleansing appliance is provided with a number of pinholes 11.

The cleansing appliance of the present invention is adapted for coupling to an adhesive wafer 20 of a body side member (not shown) for securing the appliance around the stoma on a patient's abdominal wall. The body side member thus carries matching coupling means, which in connection with this embodiment is in the form of a matching coupling ring 18.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An appliance for cleansing a surface area of the skin, said appliance being in the form of a set comprising:
    a) a body side member including an adhesive wafer for securing the appliance to the patient's skin, said wafer having an aperture for receiving a stoma, surrounding a wound, a fistula or a drainage site, and further having a first coupling element fixedly connected to the body side member; and
    b) a separately applicable cleansing appliance adapted to fit tightly against the surface of the body side member and including an inlet for injection of liquid and an outlet opening, said cleansing appliance further including,
        a front wall and a rear wall of flexible material defining an internal space there between, said rear wall being adjacent said adhesive wafer and said front wall being separated from said adhesive wafer by said rear wall and said internal space;
        the rear wall having an opening suitable for surrounding the surface area of the skin to be cleansed, said opening being surrounded by a second coupling element adapted for removable coupling and sealing to the first coupling element of the body side member;
        the front wall being provided with an adapter secured sealingly thereto, said cleansing appliance inlet being in said adapter and communicating with an opening in the front wall giving access to the internal space between the front and rear walls through the adapter, said adapter being suitable for being connected to a supply of cleansing liquid; and
    said appliance being provided with a plurality of holes that are separate from said rear and front wall openings, said holes are arranged around a perimeter of said front wall opening and are, said holes being configured in said front wall to provide a venturi effect drawing air into the cleaning appliance together with the cleansing liquid.

2. A cleansing appliance adapted to fit tightly against a skin surface of a stoma patient's body, said appliance comprising:

a front wall and rear wall of flexible material defining an internal space there between, said rear wall being nearer said skin surface than said front wall;

the rear wall having an opening suitable for surrounding a surface area of the skin to be cleansed, said opening being surrounded by a coupling element adapted for removable coupling and sealing of said appliance to a corresponding coupling element of a body side member;

the front wall being provided with an adapter secured sealingly thereto, said adapter having an inlet for injection of liquid and communicating with an opening in the front wall giving access to the internal space between the front and rear walls through the adapter, said adapter being suitable for being connected to a supply of cleansing liquid;

an outlet opening in communication with said internal space and said inlet; and said appliance being provided with a plurality of holes that are separate from said rear and front wall openings, said holes are arranged around a perimeter of said front wall opening and are, said holes being configured to provide a venturi effect drawing air into the appliance together with the cleansing liquid.

3. The cleansing appliance as claimed in claim 1, wherein the holes are small pinholes.

4. The cleansing appliance as claimed in claim 1, wherein the holes are larger than 0.2 mm in diameter.

5. The appliance as claimed in claim 1, wherein the holes have a diameter of about 0.05 mm to 0.4 mm.

6. The cleansing appliance as claimed in claim 2, wherein the holes have a diameter of about 0.05 mm to 0.4 mm.

7. The appliance as claimed in claim 1, wherein the holes have a diameter of about 0.1 mm to 0.2 mm.

8. The cleansing appliance as claimed in claim 2, wherein the holes have a diameter of about 0.1 mm to 0.2 mm.

9. The cleansing appliance as claimed in claim 2, wherein said adapter has an essentially conical shape with a top and narrow part of the cone being directed away from the patient.

10. The cleansing appliance as claimed in claim 2, wherein the holes are larger than 0.2 mm in diameter.

11. The cleansing appliance as claimed in claim 10, wherein 4 to 10 holes are present.

12. The cleansing appliance as claimed in claim 2, wherein the holes have a diameter of about 0.05 mm to 0.4 mm.

13. The appliance as claimed in claim 1, wherein said adapter has an essentially conical shape with a top and narrow part of the cone being directed away from the patient.

14. The cleansing appliance as claimed in claim 1, wherein said cleansing appliance inlet is generally circular and said holes are arranged so as to be concentric with said cleansing appliance inlet.

15. The cleansing appliance as claimed in claim 2, wherein said holes are configured in a top of the front or rear wall of the cleansing appliance to provide unobstructed air flow.

16. The cleansing appliance as claimed in claim 2, wherein said cleansing appliance inlet is generally circular and said holes are arranged so as to be concentric with said cleansing appliance inlet.

* * * * *